United States Patent
Melsheimer et al.

(10) Patent No.: US 8,043,302 B2
(45) Date of Patent: Oct. 25, 2011

(54) IMPLANT RETRIEVAL ASSEMBLY AND METHOD FOR RETRIEVING AN IMPLANT

(75) Inventors: Jeffry S. Melsheimer, Springville, IN (US); Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 764 days.

(21) Appl. No.: 11/708,235

(22) Filed: Feb. 20, 2007

(65) Prior Publication Data

US 2007/0198002 A1    Aug. 23, 2007

Related U.S. Application Data

(60) Provisional application No. 60/775,104, filed on Feb. 21, 2006.

(51) Int. Cl.
*A61B 17/26* (2006.01)
(52) U.S. Cl. ....................................................... 606/113
(58) Field of Classification Search .................. 606/108, 606/110, 113, 159, 170, 174, 205–208; 623/1.11, 623/1.23; D8/52, 54; 81/345, 347, 350, 81/351, 362, 363; 294/119; 600/201, 215–217, 600/219, 225
See application file for complete search history.

(56) References Cited

U.S. PATENT DOCUMENTS

| | | | |
|---|---|---|---|
| 2,227,270 A * | 12/1940 | Moore | 606/113 |
| 2,614,564 A * | 10/1952 | Giaccaglia et al. | 606/139 |
| 4,602,631 A | 7/1986 | Funatsu | |
| 5,234,460 A | 8/1993 | Stouder, Jr. | |
| 5,630,427 A * | 5/1997 | Hastings | 604/524 |
| 5,810,877 A | 9/1998 | Roth et al. | |
| 6,193,729 B1 * | 2/2001 | Holsinger | 606/113 |
| 6,482,178 B1 * | 11/2002 | Andrews et al. | 604/164.01 |
| 2005/0165429 A1 | 7/2005 | Douglas et al. | |

FOREIGN PATENT DOCUMENTS

| | | |
|---|---|---|
| DE | 3632786 A1 | 3/1988 |
| EP | 0 943 293 A1 | 9/1999 |
| EP | 1 066 795 A1 | 1/2001 |

OTHER PUBLICATIONS

International Search Report—PCT/US2007/004562 (Aug. 6, 2007).

* cited by examiner

*Primary Examiner* — Tom Hughes
*Assistant Examiner* — Ashley Cronin
(74) *Attorney, Agent, or Firm* — Brinks Hofer Gilson & Lione

(57) ABSTRACT

An implant retrieval frame for advancement of a retrieval device to snare an implant is disclosed. The frame comprises a first arm and a second arm. The first arm has a first handle end and a first pivot end. The second arm has a second handle end and a second pivot end. The second pivot end is connected to the first pivot end to define a pivot axis about which the first and second arm pivotally move. The frame further comprises a connector to which the retrieval device is attached. The connector is configured to cooperate with the first and second arms to translate pivotal movement of one of the first and second arms to linear movement of the retrieval device relative to the pivot point.

4 Claims, 4 Drawing Sheets

IMPLANT RETRIEVAL ASSEMBLY AND METHOD FOR RETRIEVING AN IMPLANT

CROSS-REFERENCE TO RELATED APPLICATION

This application claims the benefit of U.S. Provisional Application No. 60/775,104, filed on Feb. 21, 2006, entitled "Implant Retrieval Assembly and Method for Retrieving an Implant," the entire contents of which are incorporated herein by reference.

BACKGROUND OF THE INVENTION

The present invention is related to medical devices. More particularly, the present invention is related to implant retrieval devices and methods of retrieving an implant from a body vessel.

Implantable medical devices or medical implants continue to be improved and used for treatment in patients. For example, vena cava filters are more commonly being used for trapping blood clots and emboli in the vena cava filter to prevent pulmonary embolism. Moreover, removable baskets (e.g., stone retrieval baskets) are more commonly used for retrieving urinary calculi. Additionally, occlusion coils are commonly used to occlude aneurysms and accumulate thrombi in a body vessel.

A need for filtering devices and other medical implants arises in trauma patients, orthopedic surgery patients, neurosurgery patients, or in patients having medical conditions requiring bed rest or non-movement. During such medical conditions, the need for filtering devices may arise due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

More commonly, medical implants (e.g., vena cava filters) are being designed to be retrievable or removable. Thus, manufacturers are continuously challenged in providing improved ways of retrieving an implant. For example, although adequate, many current retrieval apparatus include a number of components to be manipulated during percutaneous introduction in a patient. In some situations, the mere number of movable components may cause difficulty to the practitioner. As a result, this may lead to additional time required in retrieving an implant in the patient.

Thus, there is a need to provide an improved way of retrieving medical implants from a body vessel of a patient.

BRIEF SUMMARY OF THE INVENTION

Embodiments of the present invention provide an implant retrieval frame, an implant retrieval assembly, and a method of retrieving an implant from a body vessel. Examples of the present invention allow for a more efficient and easier way of retrieving an implant from a body vessel. The present invention lessens amount of time required in snaring an implant from a body vessel by providing a more precise way of controlling a retrieval apparatus or assembly.

In one embodiment, the present invention provides an implant retrieval frame for advancement of a retrieval device to snare an implant. The frame comprises a first arm and a second arm. The first arm has a first handle end and a first pivot end. The second arm has a second handle end and a second pivot end. The second pivot end is connected to the first pivot end to define a pivot point or axis about which the first and second arm pivotally move. The frame further comprises a connector to which the retrieval device is attached. The connector is configured to cooperate with the first and second arms to translate pivotal movement of one of the first and second arms to linear movement of the retrieval device relative to the pivot point.

In another embodiment, the present invention provides an implant retrieval assembly for retrieval of an implant in a body vessel. The assembly comprises an implant retrieval device and the implant retrieval frame to which the implant retrieval device is attached. In one embodiment, the connector comprises first and second receivers to which the retrieval device is attached. The first receiver is connected to the first and second arms at the pivot point. The second receiver is connected to a movable body of the connector so that the connector linearly moves relative to the pivot point.

In this embodiment, the implant retrieval device comprises an outer sheath having a proximal portion and a distal portion. The device further comprises an inner catheter movably disposed through the outer sheath and a snare wire movably disposed through the inner catheter for retrieval of the implant in the body vessel. The inner catheter has a first portion and a second portion. A first side arm adapter is in communication with the proximal portion of the outer sheath and the first portion of the inner catheter for control of the outer sheath. The device further comprises a second side arm adapter in communication with the first portion of the inner catheter and the snare wire for control of the inner catheter. The second side arm adaptor is configured to be attached to the second receiver of the connector. A pin vise is in communication with the snare wire and configured to be attached to the first receiver of the connector.

In another example, the present invention provides a method of retrieving an implant from a body vessel. The method comprises percutaneously introducing the implant retrieval assembly in the body vessel. The method further comprises inserting the snare wire of the assembly to a retrieval location at which the implant is deployed in the body vessel. The method further comprises pivoting the first and second arms to linearly move the snare wire to snare the implant at the retrieval location.

Further objects, features, and advantages of the present invention will become apparent from consideration of the following description and the appended claims when taken in connection with the accompanying drawings.

DETAILED DESCRIPTION OF THE INVENTION

The present invention generally provides an implant retrieval assembly for advancement of a retrieval device to retrieve an implant deployed in a body vessel. Embodiments of the present invention generally provide an implant retrieval frame comprising first and second arms and a connector to which a snare wire and an inner catheter are attached. The first and second arms pivotally move about a pivot axis so that such movement is translated to linear movement by the connector, allowing for advancement of the inner catheter relative to the snare wire to retrieve an implant in a body vessel.

Figure 1:
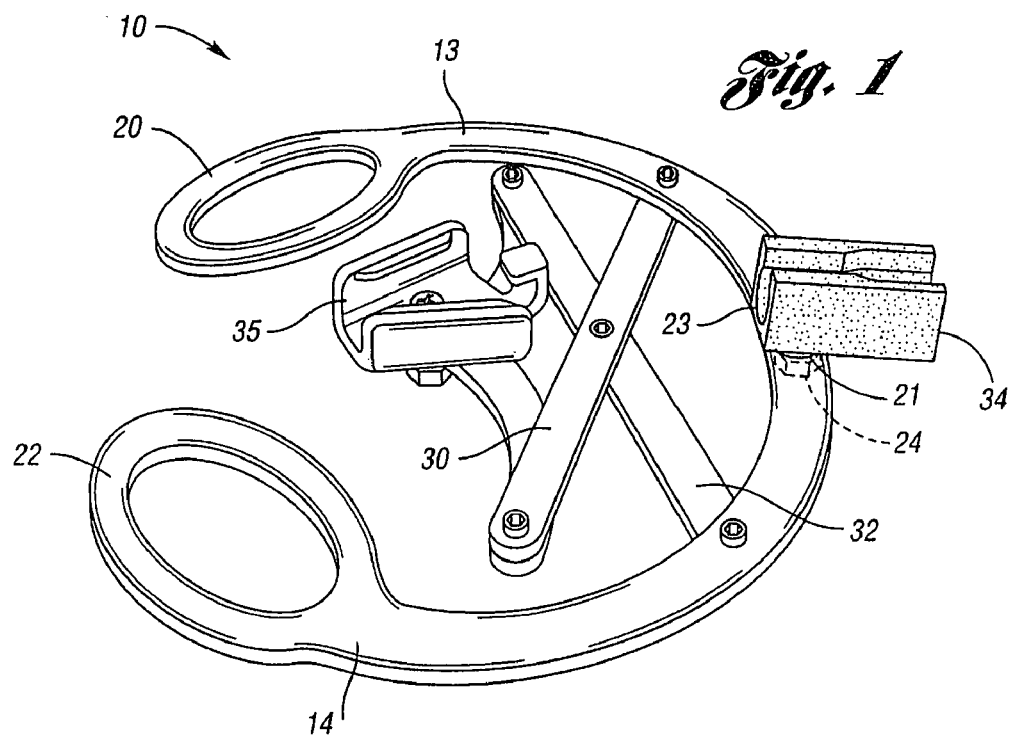
FIG. 1 is an elevated view of an implant retrieval frame in accordance with one embodiment of the present invention.

FIG. 1 illustrates an implant retrieval frame 10 for advancement of an implant retrieval device (mentioned below) to snare an implant in a body vessel in accordance with one embodiment of the present invention. As shown, the frame 10 comprises a first arm 13 and a second arm 14. The first arm 13 has a first handle end 20 that extends to a first pivot end 21. The second arm 14 has a second handle end 22 that extends to a second pivot end 23. In this embodiment, the second pivot end 23 is pivotally connected to the first pivot end 21, defining a pivot point or axis 24 about which a first and second arms 13 and 14 pivotally move.

Figure 2:
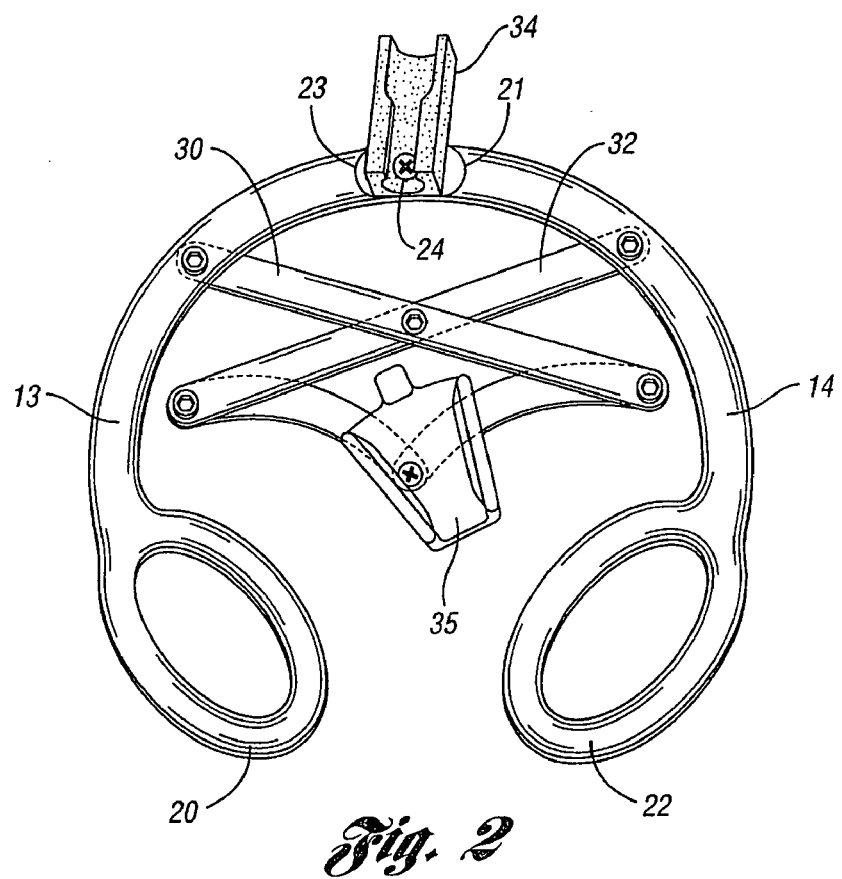
FIG. 2 is a top view of the implant retrieval frame.

As shown in FIGS. 1 and 2, the frame 10 further comprises a connector 30 to which the retrieval device (mentioned below) is attached. The connector 30 is configured to cooperate with the first and second arms 13 and 14 to translate pivotal movement of one of the arms 13 and 14 to linear movement of the retrieval device relative to the pivot point 24. That is, the connector 30 is configured to linearly extend when one of the first and second handle ends 20 and 22 pivots relative to the pivot point.

The connector 30 may comprise a plurality of subcomponents. Preferably, the connector 30 comprises a movable body 32 connected to the first and second arms 13 and 14 so that the connector linearly moves when the arms pivotally move relative to the pivot point 24. As shown, the connector 30 comprises first and second receivers 34 and 35 to which the retrieval device is attached. The first receiver 34 is connected to the first and second arms 13 and 14 at the pivot point 24. The connector 30 is connected to the movable body 32 so that the second receiver 35 linearly moves relative to the pivot point 24. This may be accomplished with a number of components as shown in the figures or with an integral component without falling beyond the scope or spirit of the present invention. In this embodiment, the first and second handle ends 20 and 22 are configured to pivot toward each other to move the movable body 32 and linearly extend the second receiver 35 from the pivot point 24. The first and second handle ends 20 and 22 are configured to pivot away from each other to retract the second receiver 35 toward the pivot point 24.

Preferably, the movement between the first and second arms 13 and 14 and the connector 30 has a predetermined ratio of movement. In this embodiment, the ratio of movement is about 1:1. The frame 10 may be comprised of any suitable material such as polymeric material, metal, or super elastic material. For example, the frame may be comprised of high density polyethylene.

In use, the implant retrieval frame 10 is configured to be received in a user's hand analogous to a pair of scissors, whereby the index finger and the thumb are inserted through the handle ends 20 and 22 of the frame 10 during retrieval of an implant in a body vessel. Pivotal movement of the handle ends 20 and 22 translates the second receiver 35 in a linear motion relative to the first receiver 34 at the pivot axis 24.

Figure 3:
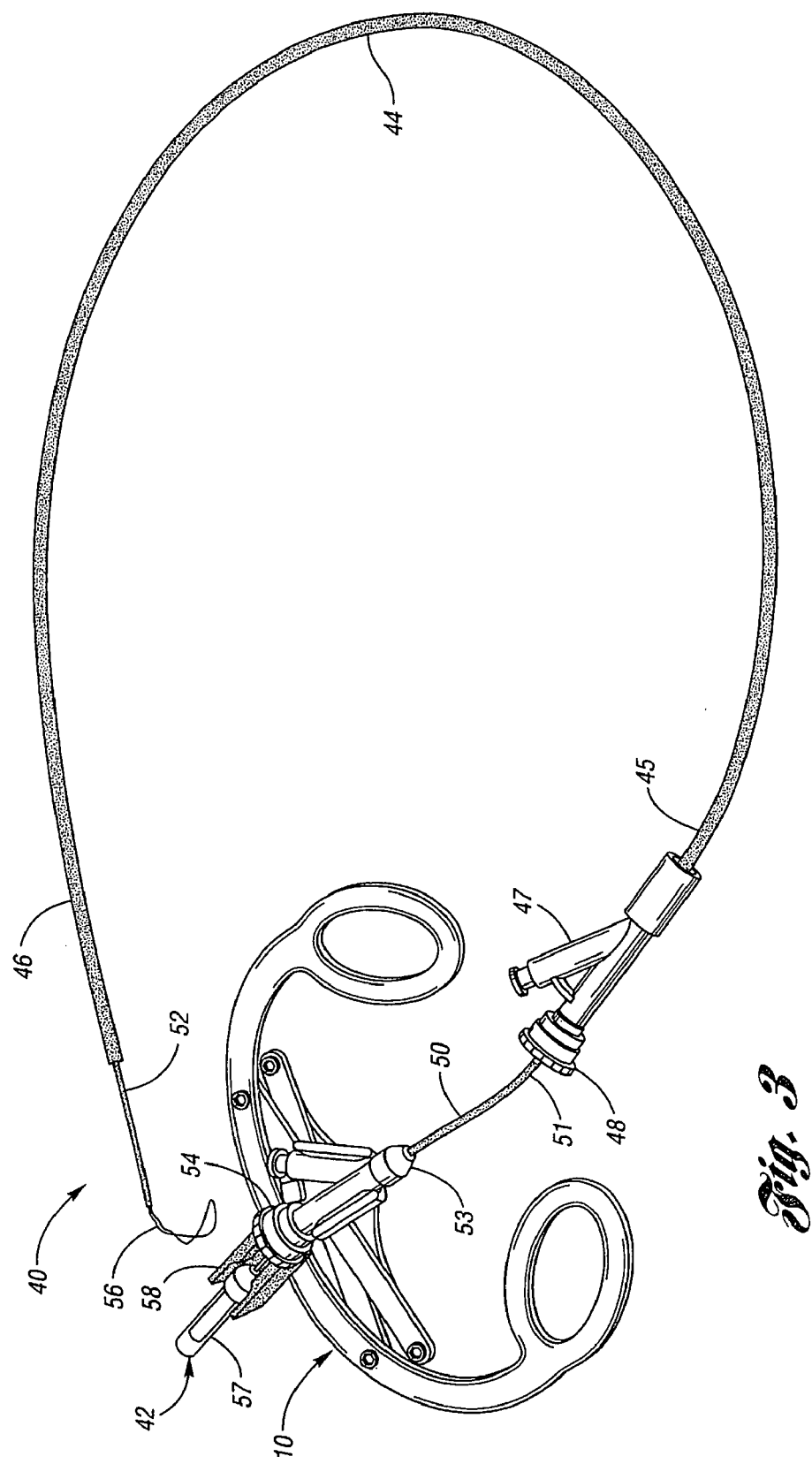
FIG. 3 is an elevated view of an implant retrieval assembly in accordance with one embodiment of the present invention.

FIG. 3 illustrates an implant retrieval assembly 40 for retrieval of an implant in a body vessel. As shown, the assembly 40 comprises an implant retrieval device 42 and the implant retrieval frame 10 for advancement of the retrieval device 42 to snare the implant. In this embodiment, the implant retrieval device 42 comprises an outer sheath 44 having a proximal portion 45 and a distal portion 46. A first side arm adaptor 47 is attached to the proximal portion 45 of the outer sheath 44 and is in fluid communication therewith. A first Touhy-Borst fitting 48 is connected to the first side arm adaptor 47 as shown for gripping an inner catheter (mentioned below). The assembly 40 further includes an inner catheter 50 having a first or proximal portion 51 and a second or distal portion 52. The inner catheter 50 is moveably disposed through the outer sheath 44 via the first Touhy-Borst fitting 48 and the first side arm adaptor 47. The first Touhy-Borst fitting 48 may be tightened on the first side arm adaptor 47 to grip and close or manipulate the first portion 51 of the inner catheter 50.

In this embodiment, a second side arm adaptor 53 is attached to the first portion 51 of the inner catheter 50 and is in fluid communication therewith. As shown, a second Touhy-Borst fitting 54 is attached to the second side arm adaptor 53. A snare wire 56 having a pin vise 57 attached to its proximal end 58 is movably disposed through the inner catheter 50 via the first and second side arm adaptors 47 and 53 for retrieval of the implant in the body vessel. The second Touhy-Borst fitting 54 may be tightened on the second side arm adaptor 53 to grip the snare wire 56 as desired.

Figure 4:
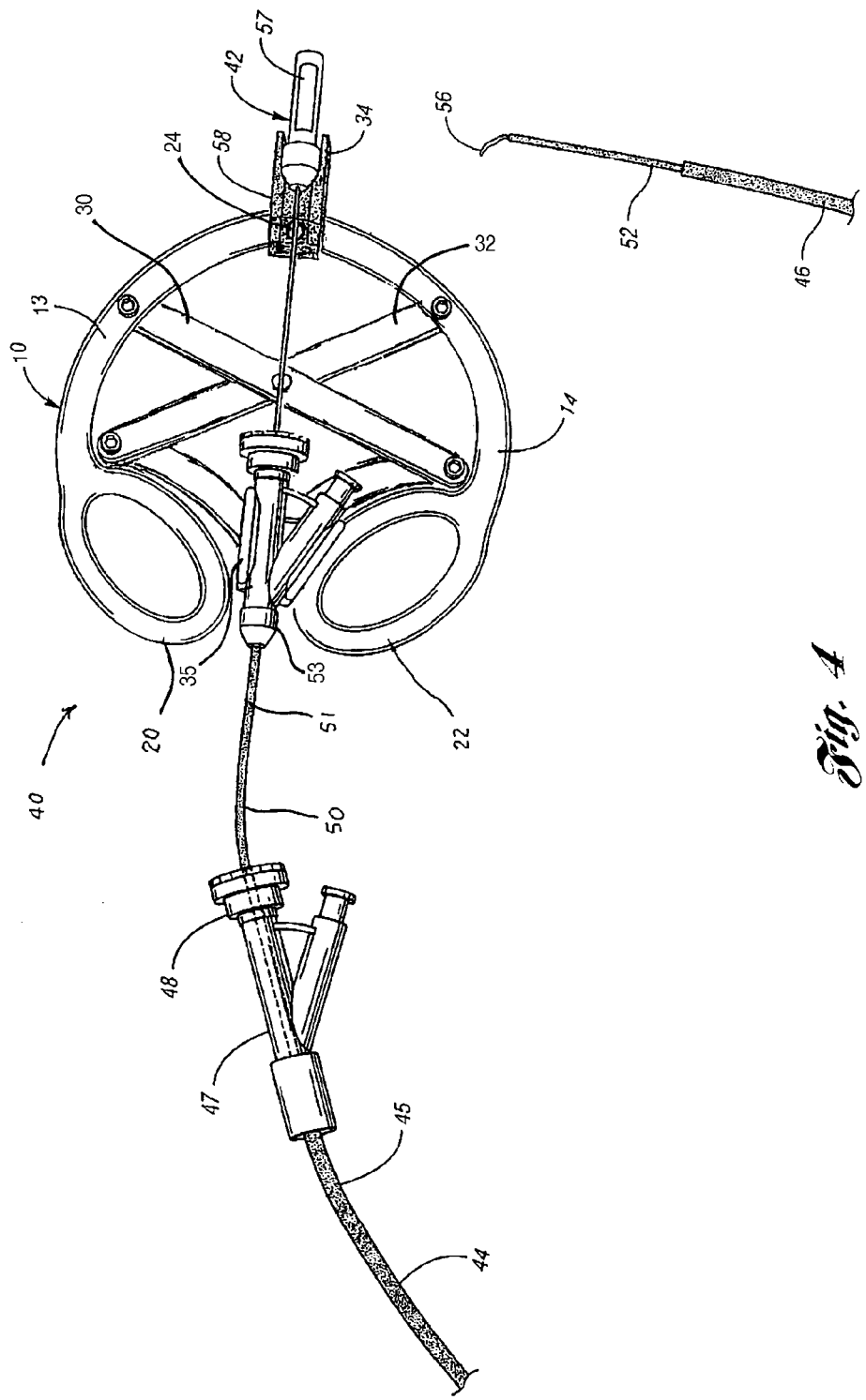
FIG. 4 is a top view of the implant retrieval assembly.

FIG. 4 illustrates the implant retrieval device 42 mounted on the implant retrieval frame 10. As shown, the second side arm adaptor 53 is configured to be mounted to the second receiver 35 of the connector 30 and the pin vise 57 is configured to be mounted to the first receiver 34 of the connector 30. In use, when the first and second arms 13 and 14 of the frame 10 pivotally move about the pivot point 24, the connector 30 cooperates therewith and is configured to linearly move relative to the pivot point 24. Thus, as the first and second arms 13 and 14 pivotally move away from each other about the pivot point 24, the second arm 14 and the second receiver 35 linearly move toward the pin vise 57 and the first receiver 34 at the pivot point 24. As a result, the inner catheter 50 is linearly retracted to deploy the snare wire 56 for contact and retrieval of the implant in the body vessel. Oppositely, as the first and second arms 13 and 14 pivot toward each other about the pivot point 24, the second side arm 14 and the second receiver 35 linearly move away from the pin vise 57 and the first receiver 34 at the pivot point 24. As a result, the inner catheter 50 rides over the snare wire 56 to retract the snare wire 56 and secure the implant within the inner catheter 50.

The assembly 40 of the present invention may be operated by a practitioner in any suitable manner. For example, the frame 10 may be operated by placing each of the index finger and the thumb through the loops of the handle ends 20 and 22 of the frame 10. This position is analogous to handling a pair of conventional scissors. Movement of the index finger and the thumb causes pivotal movement of the first and second arms 13 and 14 to translate linear movement to the second receiver 35. The second receiver 35 holds the second side arm adaptor 53 and the first receiver 34 holds the pin vise 57 to allow linear movement of the snare wire 56 relative to the inner catheter 50 when the arms 13, 14 pivot.

As a result, this embodiment of the present invention provides control of three linear movements of the assembly 40 by operation of one practitioner, providing a more time efficient, precise, and relatively easy operation of the assembly 40. For example, the first side arm adaptor 47 may be held by one of the practitioner's hand. This allows for maintaining precise stationary positioning or linear movement of the outer sheath 44. The first and second handle ends 20 and 22 may be held in the other hand of the practitioner as discussed above. This allows for linear movement of the inner catheter 50 relative to the outer sheath 44 as the practitioner's hand slides the frame 10 toward and away from the first side arm adaptor 47. Also, this allows for linear movement of the snare wire 56 relative to the inner catheter 50 as the practitioner's index finger and thumb pivot the first and second arms 13 and 14 toward and away from each other. Effectively, the assembly 40 reduces the likelihood of repositioning due to inadvertent movements and provides a relatively precise and time efficient manner in retrieving medical implants.

Figure 5:
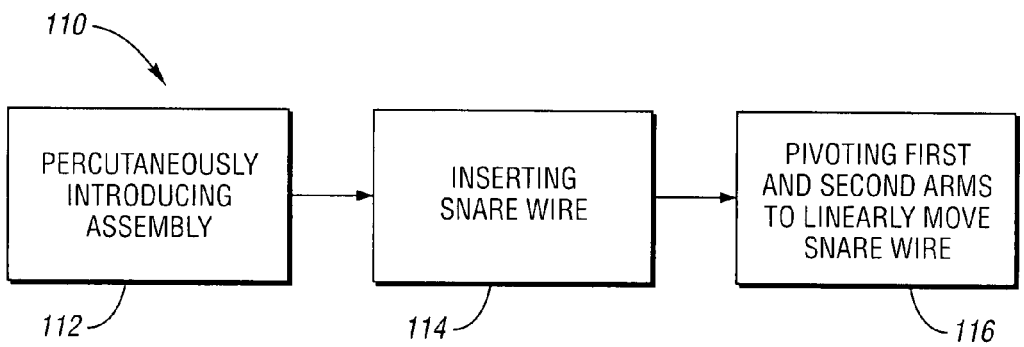
FIG. 5 is a flow chart of one method of retrieving an implant in accordance with one example of the present invention.

FIG. 5 depicts a flow chart of one method 110 for retrieval of an implant in a body vessel in accordance with one example of the present invention. The method may comprise a number of known techniques for venous access. For example, one method of the present invention may incorporate all or some steps employed in the Seldinger technique. In this example, the method 110 comprises percutaneously introducing in box 112 the implant retrieval assembly (mentioned above) in the body vessel. This may be accomplished by administering local anaesthetic to a percutaneous puncture location 70 to access a body vessel or vein 74.

Figure 6A:
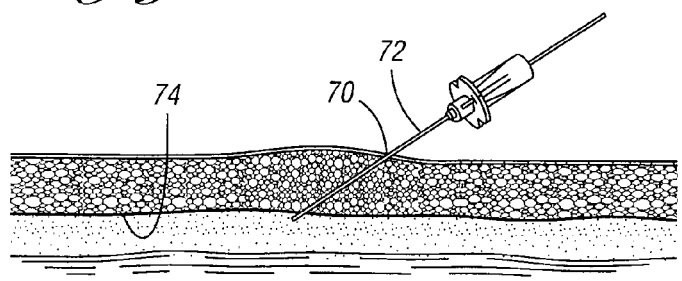
FIGS. 6A-6D are side cross-sectional views of percutaneous introduction of the assembly in accordance with one example of the present invention.

As shown in FIG. 6A, a body vessel 74 may be located by using a thin wall locator needle 72 that percutaneously punctures the skin at a percutaneous puncture location 70 to access the body vessel. The syringe of the locator needle 72 is then removed. Venous placement may be confirmed by using hemodynamic monitoring or checking for pulsatile blood flow. The needle 72 is preferably occluded to prevent air embolism or bleeding.

Figure 6B:
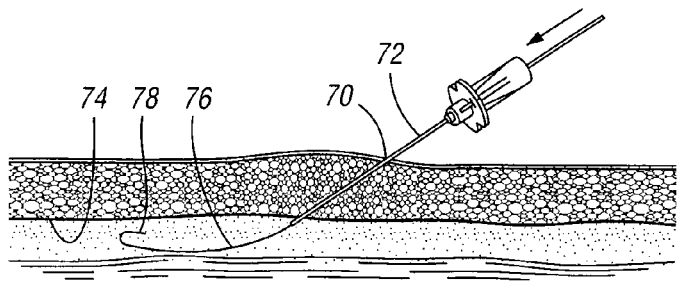
Figure 6C:
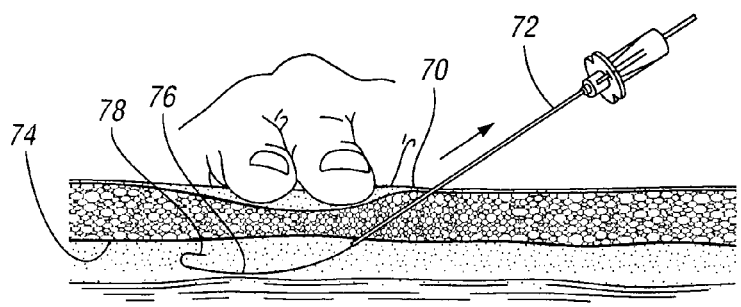

As shown in FIG. 6B, an atraumatic wire guide 76 is then introduced through the needle 72 in the body vessel 74. This may be accomplished by straightening the tip 78 of the wire guide 76 (e.g., if having a "J" tip) and advancing the wire guide 76 into the body vessel 74 through the needle 72. The needle 72 is then removed while the wire guide 76 is held stationary. Preferably, compression is maintained on the puncture to secure the wire guide 76 and lessen bleeding as depicted in FIG. 6C. The outer sheath 44 (mentioned above) is then advance over the wire guide 76 and through the percutaneous puncture location 70. If needed, the percutaneous puncture location 70 may be enlarged with a scalpel and a dilator. The outer sheath 44 serves as an introducer sheath for the introduction of the inner catheter 50 (below).

Figure 6D:
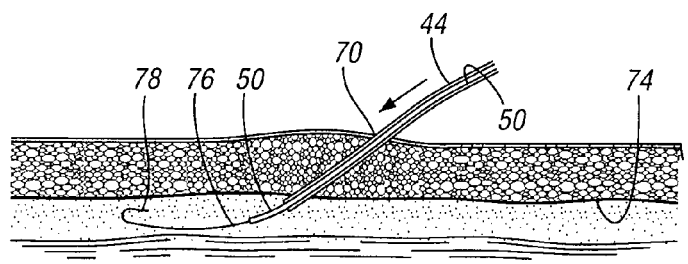

As depicted in FIG. 6D, the angiographic inner catheter 50 is then advanced over the wire guide 76. This is accomplished while the second side arm adapter 53 is attached to the second receiver 35 of the implant retrieval frame. The inner catheter 50 is pushed through the first side arm adapter and the outer sheath 44 into the body vessel 74. This may be accomplished by threading the tip of the catheter 50 over the wire guide 76 and pushing the inner catheter 50 through the outer sheath 44. In one example, the practitioner may handle the frame analogous to a pair of scissors, whereby the index finger and thumb are each placed through the loops of the handle ends. Sliding motion of the frame toward the first side arm adapter effectively pushes or threads the inner catheter through the outer sheath. Once the inner catheter is positioned in the body vessel, the inner catheter is held stationary and the wire guide may be retracted and removed from the body vessel. The lumen of the body vessel may be checked by aspiration. The location of the distal end of the inner catheter may be confirmed by x-ray.

In this example, the snare wire (mentioned above) is then inserted or further pushed in box 114 of FIG. 5 through the first side arm adapter and the inner catheter to a retrieval location in the body vessel from which the deployed medical implant is to be retrieved. During this manipulation, the inner catheter and snare wire are moved as a unit linearly in reference to the outer sheath. This may be accomplished by moving the inner catheter and frame relative to the outer sheath for advancement of the inner catheter.

The method 110 further comprises pivoting in box 116 the first and second arms to linearly move the inner catheter to contact and snare the implant from the retrieval location. The first and second arms may then be pivoted to advance and retract the inner catheter relative to the snare wire. Upon pivoting the handle ends toward each other, the distal end of the inner catheter is advanced over the snare wire for implant retrieval. The inner catheter containing the medical implant is finally retracted within the outer sheath which is then removed from the body vessel.

While the present invention has been described in terms of preferred embodiments, it will be understood, of course, that the invention is not limited thereto since modifications may be made to those skilled in the art, particularly in light of the foregoing teachings.

The invention claimed is:

1. An implant retrieval assembly for retrieval of an implant in a body vessel, the assembly comprising:

an implant retrieval device comprising;

an outer sheath having a proximal portion and a distal portion;

an inner catheter movably disposed through the outer sheath, the inner catheter having a first portion and a second portion; and a snare wire movably disposed through the inner catheter for retrieval of the implant in the body vessel; and an implant retrieval frame for advancement of the retrieval device to snare the implant, the frame comprising:

a first arm having a first handle end and a first pivot end;

a second arm having a second handle end and a second pivot end, the second pivot end connected to the first pivot end defining a common pivot axis about which the first and second arms pivotally move; and a connector to which the retrieval device is attached, the connector being configured to cooperate with the first and second arms to translate pivotal movement of one of the first and second arms to linear movement of the retrieval device relative to the pivot axis, the connector comprising a movable body connected to the first and second arms so that the connector linearly moves when the arms pivotally move relative to the pivot point, the connector further comprising first and second receivers to which the retrieval device is attached, the first receiver being connected to the first and second arms at the pivot point, the second receiver being connected to the movable body so that the connector linearly moves relative to the pivot point, the connector being configured to linearly extend when one of the first and second handles pivots towards the other relative to the pivot point and linearly retract when one of the first and second handles pivots away from the other relative to the pivot point, the first and second handles being configured to pivot towards each other to move the movable body and extend the second receiver linearly from the pivot point, wherein the first and second handles are configured to pivot away from each other to retract the second receiver towards the pivot point to allow control of linear movements of the outer sheath, the inner catheter, and the snare wire of the assembly.

2. The assembly of claim 1 wherein the implant retrieval device further comprises:
a first side arm adapter in communication with the proximal portion of the outer sheath and the first portion of the inner catheter for control of the outer sheath; and
a second side arm adapter in communication with the first portion of the inner catheter and the snare wire for control of the inner catheter, the second side arm adaptor configured to be attached to the second receiver of the connector; and
a pin vise in communication with the snare wire and configured to be attached to the first receiver of the connector.

3. The assembly of claim 1 wherein the implant retrieval frame is comprised of polymeric material.

4. The assembly of claim 1 wherein the movement between the first and second arms and the connector has a ratio of movement of about 1:1.

* * * * *